(12) United States Patent
Chang et al.

(10) Patent No.: US 9,662,295 B2
(45) Date of Patent: May 30, 2017

(54) COMPOSITION CONTAINING TEA WATER FOR SUPPRESSING AGING OF SKIN

(71) Applicant: AMOREPACIFIC CORPORATION, Seoul (KR)

(72) Inventors: Hui Kyoung Chang, Yongin-si (KR); Se Jin Yoo, Yongin-si (KR); Chan Su Rha, Yongin-si (KR); Seok Yun Baek, Yongin-si (KR); Joo Yeon Kim, Yongin-si (KR); Mi Suk Yang, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 217 days.

(21) Appl. No.: 14/409,788

(22) PCT Filed: Apr. 26, 2013

(86) PCT No.: PCT/KR2013/003646
§ 371 (c)(1),
(2) Date: Dec. 19, 2014

(87) PCT Pub. No.: WO2014/003304
PCT Pub. Date: Jan. 3, 2014

(65) Prior Publication Data
US 2015/0238411 A1 Aug. 27, 2015

(30) Foreign Application Priority Data
Jun. 29, 2012 (KR) .................. 10-2012-0070454

(51) Int. Cl.
A61K 36/00 (2006.01)
A61K 8/97 (2017.01)
A61K 36/82 (2006.01)
A61Q 19/08 (2006.01)

(52) U.S. Cl.
CPC ............... *A61K 8/97* (2013.01); *A61K 36/82* (2013.01); *A61Q 19/08* (2013.01)

(58) Field of Classification Search
None
See application file for complete search history.

(56) References Cited

U.S. PATENT DOCUMENTS

2005/0287278 A1* 12/2005 Quan et al. .................. 426/597

FOREIGN PATENT DOCUMENTS

| KR | 1020070106175 A | 11/2007 |
| KR | 1020100121352 A | 11/2010 |
| KR | 1020110060857 A | 6/2011 |
| KR | 1020120017987 A | 2/2012 |

OTHER PUBLICATIONS

Hsu, Stephen, Green tea and the skin, J Am Acad Dermatol, vol. 52, No. 6, Jun. 2005, pp. 1049-1059.
International Search Report for International Application No. PCT/KR2013/003646 dated Jul. 18, 2013.
Wei, et al., Protective Effects of Tea Polysaccharides and Polyphenols on Skin, Journal of Agricultural and Food Chemistry, 2009, vol. 57, No. 17, pp. 7757-7762.
Written Opinion for International Application No. PCT/KR2013/003646 dated Jul. 18, 2013.

* cited by examiner

*Primary Examiner* — Qiuwen Mi
(74) *Attorney, Agent, or Firm* — Cantor Colburn LLP

(57) ABSTRACT

The present invention discloses a composition for suppressing the aging of skin, which contains tea water derived from fresh tea leaves having inactivated enzymes. The composition containing tea water according to the present disclosure may inhibit the activities of matrix metalloproteinase (MMP) and elastase, stimulate the production of collagen by increasing its expression, suppress the formation of skin wrinkles, and reduce the formed skin wrinkles. Furthermore, it has an excellent effect of suppressing skin aging.

7 Claims, 10 Drawing Sheets

COMPOSITION CONTAINING TEA WATER FOR SUPPRESSING AGING OF SKIN

CROSS-REFERENCE TO RELATED APPLICATION

This application claims priority to Korean Patent Application No. KR 10-2012-0070454, filed on Jun. 29, 2012, and all the benefits accruing therefrom under 35 U.S.C. §119, the contents of which in its entirety are herein incorporated by reference.

BACKGROUND

1. Field

The present disclosure relates to a composition containing tea water for suppressing or alleviating skin aging.

2. Description of the Related Art

The connective tissue of the skin is mainly composed of collagen and elastin. Since the collagen and the elastin give elasticity to the skin, the skin is easily damaged and ages if they are weakened. Matrix metalloproteinases (MMPs) and elastase are enzymes that are involved in the breakdown of the collagen and the elastin. As the skin ages, the expressions of MMPs and the elastase increase and the increased MMPs and the elastase break down the collagen and the elastin of the skin. As this mechanism is repeated, the skin develops wrinkles and ages earlier. Thus, if break down of the MMPs and the elastase can be suppressed and collagen formation can be stimulated, skin wrinkles would be suppressed and improved and skin aging would be suppressed.

REFERENCES OF THE RELATED ART

Korean Patent Publication No. 10-2010-0121352 (2010.11.17.).

SUMMARY

The present disclosure is directed to providing a composition having excellent skin aging suppression effect by suppressing formation of skin wrinkles and improving the formed skin wrinkles.

In one aspect, there is provided a composition containing tea water, which is derived from fresh tea leaves whose enzymes are inactivated, for suppressing skin aging.

In another aspect, there is provided a cosmetic or pharmaceutical composition containing tea water, which is derived from fresh tea leaves whose enzymes are inactivated, for suppressing skin aging.

The composition containing tea water according to the present disclosure may inhibit the activities of matrix metalloproteinase (MMP) and elastase, stimulate the production of collagen by increasing its expression, suppress the formation of skin wrinkles, and reduce the formed skin wrinkles. Furthermore, it has an excellent effect of suppressing skin aging. And, the composition not actually containing ions may be easily applied to a cosmetic composition or a pharmaceutical composition. Further, the composition has a small amount of skin irritating ingredients, and thus a person of delicate skin may feel free to use the composition.

DETAILED DESCRIPTION

Figure 1:
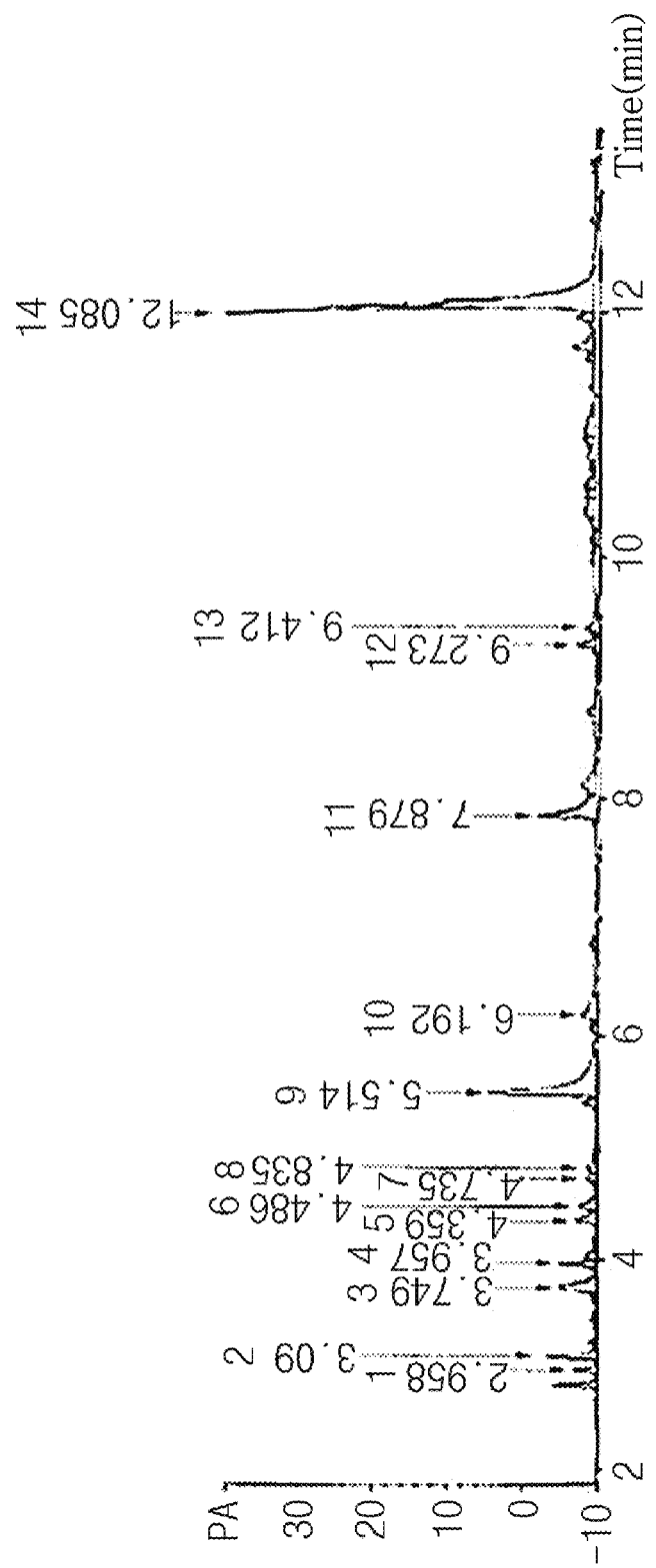
FIG. 1 is a graph showing the result of quantitative analysis of Example 1 using gas chromatography.

Herein, the term "skin" refers to the tissues covering the surface of the animal's body, and is the broadest concept including not only tissues covering the surface of the body such as the face or trunk but also the scalp and hair.

One aspect of the present disclosure provides a composition containing tea water, which is derived from fresh tea leaves whose enzymes are inactivated, for suppressing skin aging. Another aspect of the present disclosure provides a composition containing tea water, which is derived from fresh tea leaves whose enzymes are inactivated, for suppressing or improving skin wrinkles.

In still another aspect of the present disclosure, the tea water derived from fresh tea leaves whose enzymes are inactivated, described above, may be used for suppressing skin aging. Further, the present disclosure may provide a method for suppressing skin aging, which includes administering the tea water derived from fresh tea leaves whose enzymes are inactivated as an active ingredient to a subject in an effective amount.

Furthermore, still further another aspect of the present disclosure may provide tea water derived from inactivated fresh tea leaves for being used for skin aging suppression.

Herein, the term "aging" refers to decaying change phenomenon of the body, which happens to people when they become older, and includes deterioration of physiological activity and metabolism in the body, and skin aging. The skin aging includes the state that wrinkles are formed and regenerative ability is lost.

Herein, the term "tea leaves" refers to buds or leaves of *Camellia sinensis* regardless of the quality or type thereof. Specifically, any of spring tea, summer tea and autumn tea according to harvest time may be used, but not limited thereto. Herein, the term "fresh tea leaves" refers to non-processed tea leaves.

Herein, the term "tea water" refers to liquid originated from the fresh tea leaves, and specifically, it includes tea juice obtained by extracting the fresh tea leaves, or water or alcohol extract of the fresh tea leaves. The tea water according to the present disclosure is different from general green tea water, which is obtained by infusing dried tea leaves in liquid such as water, because it is liquid obtained from undried tea leaves. The tea water according to one aspect of the present disclosure contains ingredients helpful to humans as well as water contained in tea leaves.

In one aspect of the present disclosure, the tea water includes "non-ionic" tea water. In another aspect of the present disclosure, the non-ionic tea water includes tea water, which does not actually contain ions. In still another aspect of the present disclosure, the tea water, which does not actually contain ions, includes tea water, which has ion concentration of 0.01 ppm or less, specifically, 0.001 ppm or less, more specifically, 0.0001 ppm or less.

Generally, when manufacturing a cosmetic composition, ion-purified water having fewer kinds and a small amount of ions is used, because if the ions are contained in a large amount, they may inhibit effects of a composition containing surfactants, emulsifier and the like, and affect to stability of the composition. Further, because a large quantity of ions has the property of lowering viscosity of the viscous composition with time, it is not appropriate to be contained in a cosmetic composition. In general, liquid obtained by infusing processed tea leaves contains $F^-$, $Cl^-$, $NO_3^-$, $PO_4^-$ and $SO_4^-$ at a concentration of 100 to 3000, 500 to 2500, 0 to 200, 200 to 5000, 50 to 3000 µg per 100 g of water, respectively. Accordingly, in consideration that such ions are contained in the liquid obtained by infusing processed tea leaves, in order to be used for a cosmetic composition, the concentration of the liquid may be very low by infusing the tea leaves in water for a time as short as possible, not the concentration suitable for drinking. In this case, it may be difficult that useful ingredients contained in tea are contained in the liquid obtained by infusing tea leaves. On the other hand, the composition according to one aspect of the present disclosure containing non-ionic tea water, wherein ions are already removed, may be easily applied to a cosmetic or pharmaceutical composition.

In one aspect of the present disclosure, the tea water includes tea water, which satisfies at least one of the linalool concentration of 5 µg/ml or less, the hexanol concentration of 0.2 µg/ml or less and the z-3-hexenol concentration of 0.2 µg/ml or less. In another aspect of the present disclosure, the tea water includes tea water, which satisfies at least one of the linalool concentration of 2 µg/ml or less, specifically 1.5 µg/ml or less, the hexanol concentration of 0.1 µg/ml or less, specifically 0.05 µg/ml or less, and the z-3-hexenol concentration of 0.15 µg/ml or less, specifically 0.1 µg/ml or less. The tea water according to the present disclosure, which contains skin irritating ingredients in a small quantity as mentioned above, is suitable for an ingredient of a composition, which is applied to the skin, such as a cosmetic or a pharmaceutical composition.

In one aspect of the present disclosure, the tea water includes tea water, which is manufactured by a method including: obtaining tea juice by inactivating enzymes of fresh tea leaves and then extracting juice; and obtaining non-ionic tea water by removing ions from the tea juice obtained in the above step. The tea water manufactured by the above method actually does not contain ions, thereby it may be easily applied to a cosmetic or a pharmaceutical composition.

In one aspect of the present disclosure, the fresh tea leaves may be subjected to pretreatment before obtaining the tea juice, and it may include: harvesting tea leaves, washing thereof with purified water to remove impurities, and removing water droplets attached to the surface of the tea leaves by using adewatering equipment. Then, the tea leaves may be stored at a low temperature (4 to 10° C.) for offsetting heat generated from the tea leaves.

In the step of obtaining tea juice in one aspect of the present disclosure, enzymes of the fresh tea leaves may be inactivated by steam treatment, heat treatment or high pressure treatment. When steaming the fresh tea leaves, steaming may be conducted at a temperature of 100 to 150° C., specifically 102 to 121° C., and more specifically 105 to 112° C.

In one aspect of the present disclosure, the method for extracting the fresh tea leaves, in the step of obtaining tea juice by extracting the fresh tea leaves whose enzymes are inactivated, includes at least one method selected from the group consisting of gear-type extraction using compression effect, press-type extraction, crush-type extraction and enzyme degradation-type extraction.

In another aspect of the present disclosure, after the tea juice is obtained, the obtained tea juice may be further passed through a sieve. Through this step, residual solids of the tea juice are removed. In one aspect of the present disclosure, the size of the sieve may be 10 to 400 mesh. In another aspect of the present disclosure, the size of the sieve may be 30 to 200 mesh. In further another aspect of the present disclosure, the size of the sieve may be 80 to 120 mesh.

In the step of obtaining tea water in one aspect of the present disclosure, ions are removed by evaporating and liquefying, or percolating the tea juice. Through this, the ions, which interrupt the effect of a cosmetic composition or affect to its stability, may be removed from the tea juice. Evaporation of the tea juice may be conducted by heating the tea juice at a temperature of about 100 to about 121° C. under pressure. The heating may be conducted at a temperature of about 80 to about 100° C. under atmospheric pressure. The heating may be conducted at a temperature of about 40 to about 80° C. under reduced pressure.

In one aspect of the present disclosure, after obtaining the tea water by removing ions from the tea juice, isolating and removing undesirable ingredients by centrifugation, membrane separation or distillation separation of the tea water obtained in the above step may be further conducted. In another aspect of the present disclosure, the step of isolating and removing may include adding an organic solvent to the obtained tea water in a predetermined amount, and then selectively removing the organic solvent by distillation, so as to select ingredients having low preference or undesired and then isolating and removing thereof. In one aspect of the present disclosure, the organic solvent may be $C_1$ to $C_5$ alcohol, and specifically ethyl alcohol. The organic solvent may be added in an amount of 5 to 40 wt %, based on the total weight of the tea water.

In one aspect of the present disclosure, after obtaining the tea water, maturing the obtained tea water may be further contained. Through this maturation, the skin irritating ingredients such as hexanol, z-3-hexenol or linalool may be removed better. In the step of maturing the obtained tea water, the maturation may be conducted at 0 to 120° C. for 12 to 24 hours. In another aspect of the present disclosure, the maturation may be conducted at 80 to 120° C. under pressure for 12 to 24 hours, under the condition that moisture of the tea water does not evaporate. In further another aspect of the present disclosure, the maturation may be conducted at 40 to 80° C. under atmospheric pressure for 12 to 24 hours. In still further another aspect of the present disclosure, the maturation may be conducted at 4 to 40° C. under reduced pressure for 12 to 24 hours.

According to one aspect of the present disclosure, the composition may contains the tea water in an amount of 10 to 90 volume %, specifically 20 to 80 volume %, and more specifically 30 to 70 volume %, based on the total volume of the composition. Containing the tea water with the above mentioned volume % is not only suitable for expressing the desired effect of the present disclosure but also enable to satisfy both of stability and safety of the composition, and may be also suitable in the term of the effect over the cost. Specifically, the composition containing tea water of the above mentioned volume % has excellent effects of promoting collagen synthesis and inhibiting activities of MMPs and elastase. Furthermore, it may have better effects of suppressing and improving skin wrinkles, and suppressing aging. In addition, it may have low skin irritation and cytotoxicity.

According to one aspect of the present disclosure, the composition containing tea water for suppressing skin aging includes a cosmetic composition. In another aspect of the present disclosure, the tea water may be contained in the cosmetic composition as a base solution or a major active ingredient.

The cosmetic composition may be provided as all formulations suitable for local application. For example, it may be provided as a composition formulation of solution, emulsion obtained by dispersing oil phase in water phase, emulsion obtained by dispersing water phase in oil phase, suspension, solid, gel, powder, paste, foam or aerosol. The composition of these formulations may be prepared by a method commonly employed in the art.

Within the range not damaging the main effect and specifically increasing the main effect, the cosmetic composition may contain other ingredients other than the above materials. The cosmetic composition according to the present disclosure may contain a material selected from the group consisting of vitamin, polymer peptide, polymer polysaccharide and sphingolipid. Further, the cosmetic composition according to the present disclosure may contain humectants, emollients, surfactants, UV absorbing agents, preservatives, disinfectants, anti-oxidizing agents, pH modifiers, organic and inorganic pigments, perfumes, cooling agents or antiperspirants. The mixing ratio of the above ingredients may be easily selected by a person of ordinary skill in the art within the range not damaging the objects and effects of the present disclosure.

The composition containing tea water for suppressing skin aging according to one aspect of the present disclosure includes a pharmaceutical composition. In another aspect of the present disclosure, the tea water may be contained as a base solution or a major active ingredient of the pharmaceutical composition.

The pharmaceutical composition according to one aspect of the present disclosure may be administered orally, parenterally, intrarectally, topically, transdermally, intravenously, intramuscularly, intraperitoneally or subcutaneously. Formulations for oral administration may be in the form of tablet, pill, soft and hard capsule, granule, powder, fine granule, liquid, emulsion or pellet, but not limited thereto. Formulations for parenteral administration may be solution, suspension, lotion, gel, injectable solution, drop, suppository, patch or sprays, but not limited thereto. These formulations may be prepared easily by a method commonly employed in the art, and surfactant, vehicle, hydrating agent, emulsification accelerator, suspension, salt or buffer for osmotic pressure control, colorant, flavor, stabilizer, antiseptic, preservative or other commonly used adjuvants may be used adequately.

The administration dosage of the active ingredient of the pharmaceutical composition according to the present disclosure may vary depending on the age, gender and body weight of a subject to be administered, pathological condition and severity thereof, administration route and discretion of a diagnoser. Determination of the administration dosage considering these factors is in the level of those skilled in the art. A daily dosage thereof may be, for example, 0.1 to 5000 mg/kg/day, more specifically 50 to 500 mg/kg/day, but is not limited thereto.

One aspect of the present disclosure provides a kit including: the composition containing tea water derived from fresh tea leaves whose enzymes are inactivated; and directions disclosing that the composition is applied to a subject for 80 hours to 200 hours. In another aspect of the present disclosure, the directions may include content that the composition is applied to a subject for 90 hours to 150 hours. In order to exert effects of tea water such as enough anti-aging, anti-wrinkle and wrinkle-free effects on the skin to a subject, it is needed to apply the composition for at least a certain time period, and in terms of convenience increase and expression of effect over time, the time for application may be limited.

EXAMPLES

The examples (and experiments) will now be described. The following examples (and experiments) are for illustrative purposes only and not intended to limit the scope of the present disclosure.

Example 1

Preparation of Tea Water 2 kg of fresh tea leaves (Jeju Sulloc-Tea, Okloc $2^{nd}$ crop tea), which are harvested within several hours, are contacted to steam generated at 100° C. for 2 to 3 min for enzyme inactivation, inserted into a two screw-type juice extractor, and then separated into tea juice and tea solids. The tea juice is filtered through an 80-mesh sieve to remove residual solid matters. The tea juice is put into a vacuum concentrator, distillated at 40 to 80° C., and the generated steam is cooled so as to obtain tea water. The obtained tea water is sterilized and packaged with a 0.2-micrometer sterilization filter in an aseptic clean bench so as to prepare Example 1.

Comparative Examples 1 and 2

20 g of tea leaves, which are harvested around the same time with the fresh tea leaves used for preparing Example 1, and firstly processed through steaming-primary drying and roasting-rolling-middle drying and roasting-final drying and roasting-drying processes, are soaked in 70° C. purified water for 2 min, and then filtered through a 200-mesh sieve so as to prepare Comparative Example 1. The firstly processed tea leaves are secondly processed through heating-sieving-cutting-stem selection-mixing processes, 20 g of the secondly processed tea leaves are soaked in 70° C. purified water for 2 min, and then filtered through a 200-mesh sieve so as to prepare Comparative Example 2.

Test Example 1

Evaluation of Ingredients of Composition

Example 1, Comparative Example 1 and Comparative Example 2 are subjected to gas chromatography analysis by solid phase microextraction (SPME). Gas chromatogram showing the result of quantitatively analyzing Example 1 is shown in FIG. 1 and the following Table 1.

TABLE 1

| No. | Retention Time (min) | Compound |
|---|---|---|
| 1 | 2.958 | Hexanol |
| 2 | 3.09 | 2-Propanone |
| 3 | 3.749 | 3-Butane |
| 4 | 3.957 | 2-Ethoxy-2-methyl propane |
| 5 | 4.359 | 3-Methyl butanal |
| 6 | 4.486 | 2-Methyl butanal |
| 7 | 4.735 | 1-Penten-3-ol |
| 8 | 4.835 | Tetrahydro-2,2,5,5-tetramethyl furan |
| 9 | 5.514 | 3-Butyronitrile |
| 10 | 6.192 | 1-Pentanol |
| 11 | 7.879~8.119 | z-3-Hexenol |
| 12 | 9.273 | 4-Hydroxy-4-methyl-2-pentanone |
| 13 | 9.412 | 4-Methyl-2-heptanone |
| 14 | 12.085 | Linalool |

Among the main ingredients of tea, those having a low sensory threshold and thus allowing humans to distinguish them immediately include the following three ingredients: hexanol, z-3-hexenol and linalool. Among them, the linalool is known to cause allergy upon direct contact with the skin. In the result of gas chromatography analysis of Example 1, the three ingredients having the low sensory

TABLE 2

| Material | Retention Time (min) | Peak Area | Concentration (µg/ml) |
|---|---|---|---|
| Hexanol | 2.958 | 6.22 | 0.04 |
| z-3-Hexenol | 7.879-8.119 | 44.14 | 0.14 |
| Linalool | 12.085 | 156.02 | 1.21 |

As shown in the above Table, the tea water of Example 1 contains the skin irritating ingredient only in a trace amount, i.e., z-3-hexenol concentration of 0.2 µg/ml or less, hexanol concentration of 0.2 µg/ml or less and linalool concentration of 5 µg/ml or less.

Figure 2:
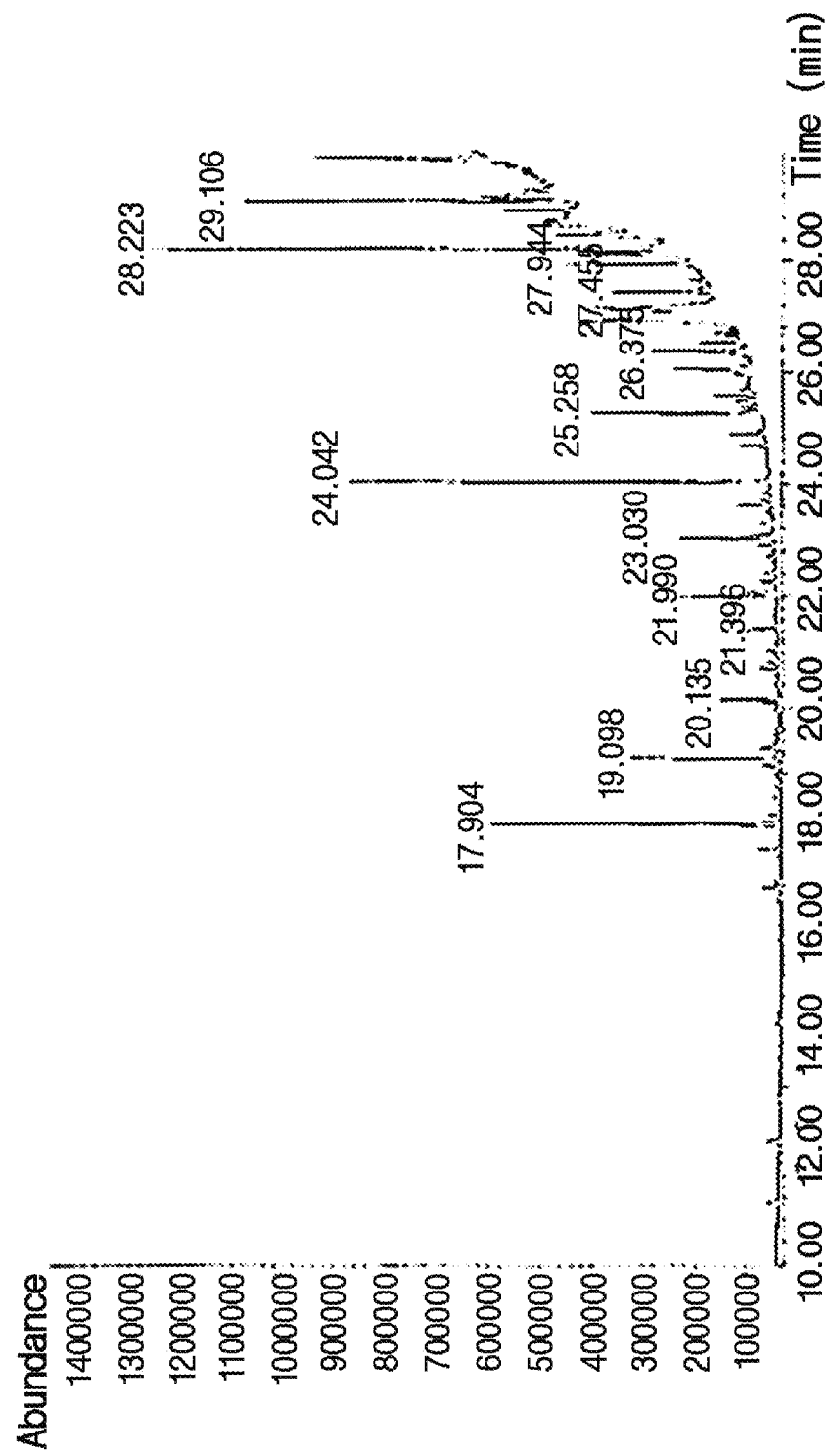
FIG. 2 is a graph showing the result of qualitative analysis of Comparative Example 1 using gas chromatography.
Figure 3:
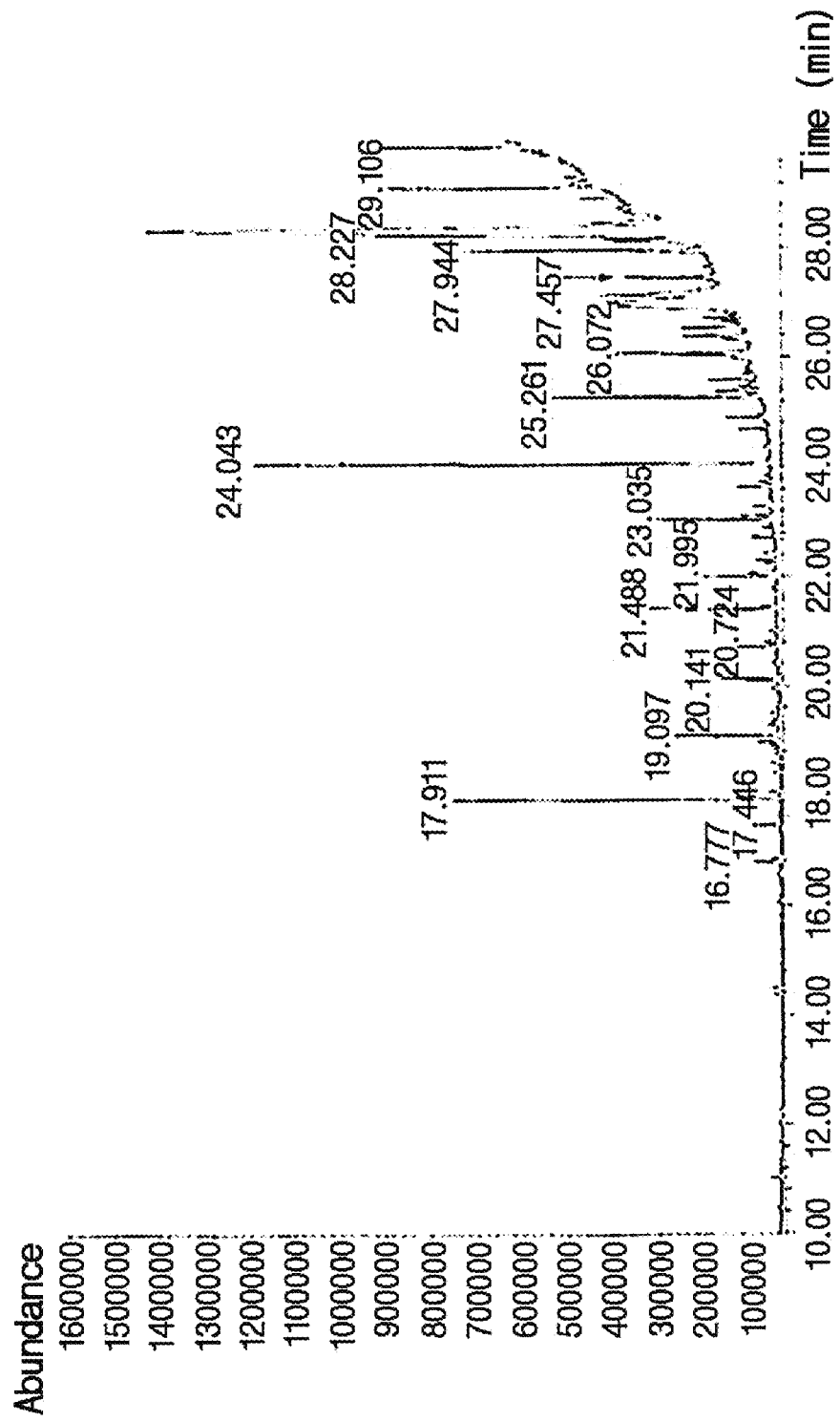
FIG. 3 is a graph showing the result of qualitative analysis of Comparative Example 2 using gas chromatography.
Figure 4:
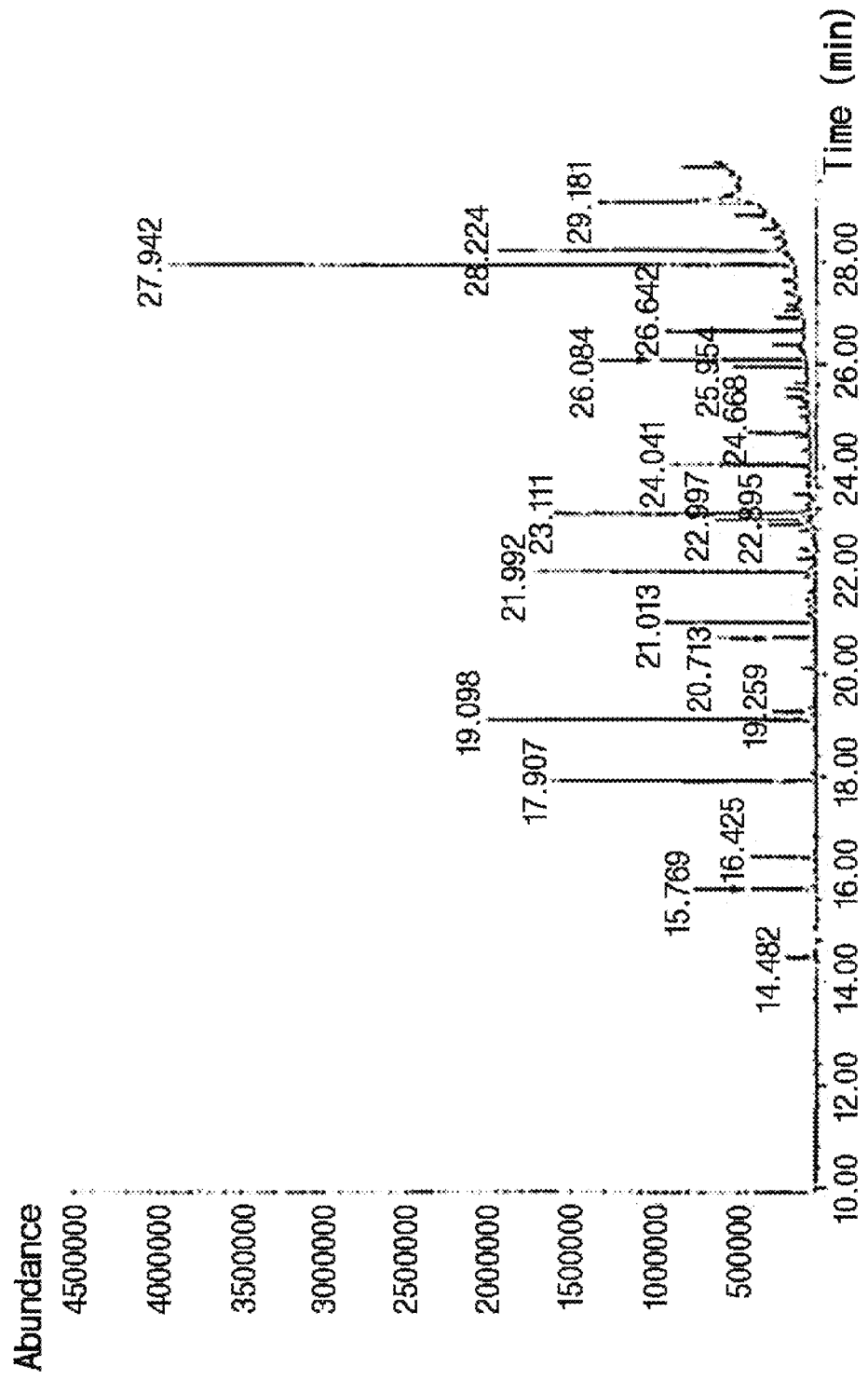
FIG. 4 is a graph showing the result of qualitative analysis of Example 1 using gas chromatography.

Meanwhile, gas chromatograms showing the results of qualitatively analyzing Comparative Examples 1 and 2 are shown in FIG. 2 and FIG. 3, and gas chromatogram showing the result of qualitatively analyzing the tea water of Example 1 is shown in FIG. 4. Name of ingredients corresponding to the peaks of FIG. 4 are shown in the following Table. Referring to FIG. 2 and FIG. 3, there are some peaks that are not present in FIG. 4, and it is thought that the peaks are derived from pyrazine-like aromatic ingredients, which are generated by modification of the unique ingredients of fresh tea leaves. Such ingredients may cause skin irritation, and thus those are not suitable for a cosmetic composition or a pharmaceutical composition.

TABLE 3

| Retention Time (min) | Compound |
|---|---|
| 14.482 | z-3-Hexenol |
| 15.769 | Trans linalool |
| 16.425 | Linalool oxide A |
| 17.907 | 1,6-Octadien-3-ol |
| 19.098 | Carbitol |
| 20.713 | Linalool oxide D |
| 21.013 | 2H-pyran-3-ol |
| 21.992 | Linalool |
| 22.895 | 1,4-Butanodiol |
| 22.997 | Benzyl nitrile |
| 23.111 | Jasmone |
| 24.668 | Buryrated hydroxytoluene |
| 25.954 | Mulool |
| 27.942 | Indole |
| 28.224 | Benzophenone |

Thus, the tea water according to the present disclosure contains the skin irritating ingredient in a trace amount. Thus, it is suitable for an ingredient of a cosmetic or pharmaceutical composition.

Test Example 2

Basic Analysis

Basic ingredient analysis against the tea water of Example 1 is carried out to determine pH, refractive index, specific gravity, heavy metal content, count of bacteria and the like, and the results are shown in the following Table.

TABLE 4

| Analysis Item | Example 1 |
|---|---|
| pH | 5.82 |
| Refractive Index | 1.333 |
| Specific Gravity | 1.002 |
| Lead | 0.0760 mg/kg |
| Arsenic | 0.0674 mg/kg |
| Bacteria Number | 12/ml |
| Fungus Number | Not detected |

As can be seen from the above, the tea water of Example 1 satisfies standard for a cosmetic composition.

Test Example 3

Cytotoxicity Test (1) Cell Culture

Human fibroblast cells are prepared by culturing in a Dulbecco's Modified Eagle Medium (DMEM) containing penicillin/streptomycin 100 units/ml and 10% FBS in a 5% $CO_2$ incubator at 37° C.

(2) Preparation of Medium Containing Tea Water

Mediums containing tea water in an amount of 50% (v/v) and 100% (v/v) are prepared, respectively. Specifically, the medium containing 100% tea water is prepared by mixing DMEM powder (GIBCO, New York, USA) to the tea water of Example 1, and then adding antibiotics (penicillin/streptomycin 100 units/ml) and 10% FBS. The medium containing 50% tea water is prepared by mixing the tea water of Example 1 and deionized water to the volume ratio of 1:1, mixing DMEM powder thereto, and then adding antibiotics (penicillin/streptomycin 100 units/ml) and 10% FBS.

(3) Test of Cytotoxicity by Tea Water

The human fibroblast cells prepared in (1) is added to a 24-well plate and cultured for 24 hours, and then the medium is replaced with a serum-free medium. Then, the DMEM mediums prepared in (2), which contain 50% (v/v) and 100% (v/v) tea water, respectively, are added thereto, and then cultured for 24 hours. After culturing for 24 hours, dimethyl thiazolyl diphenyl tetrazolium salt (MTT) solution of 5 mg/ml is added thereto, and further cultured for 4 hours in a 37° C. incubator. After culturing, supernatant is removed, and then DMSO is added to formazan formed by reduction of MTT to lyse cells. Then, absorbance is measured at 540 nm by using an enzyme-linked immuno sorbent assay (ELISA) microplate reader (SoftMax Pro5, Molecular Devices, USA). Cells treated with a DMEM medium not containing the tea water are used as a control group, and cytotoxicity level (%) compared to the control group is evaluated. The results are shown in FIG. 5.

Figure 5:
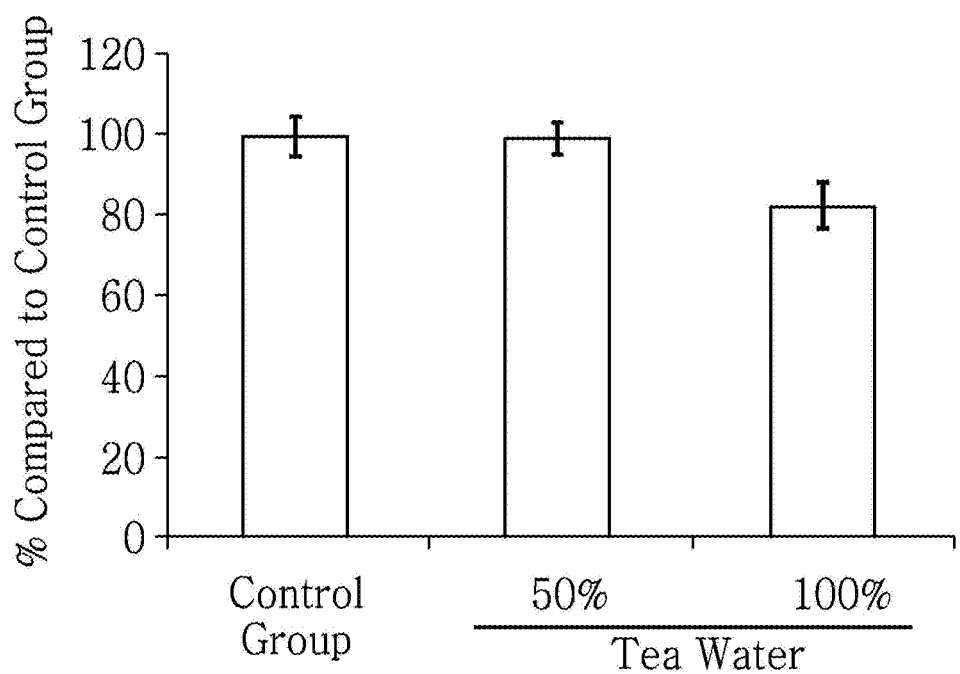
FIG. 5 is a graph showing the result of evaluating cytotoxicity by tea water.

As can be seen in FIG. 5, the cells treated with 100% (v/v) tea water show 15% cytotoxicity, but the cells treated with 50% (v/v) tea water does not show cytotoxicity.

Test Example 4

Confirmation of Collagen Expression by Tea Water

The human fibroblast cells prepared in (1) of Test Example 3 are added to a 24-well plate and cultured for 24 hours, and then the medium is replaced with a serum-free medium. After 24 hour-starvation, the DMEM medium (Control group) and the DMEM medium prepared in (2) of Test Example 3 containing 50% (v/v) tea water are added thereto, respectively, and then cultured for 120 hours. After culturing, protein of each cell is analyzed by SDS-PAGE analysis method. 10 μg of protein quantified using a Bio-Rad reagent is subjected to 10% SDS-PAGE, and then the protein on a gel is blotted to a PVDF membrane. After blocking the membrane with 5% skim milk, the membrane is reacted with primary antibodies of collagen I and GAPDH 1, and then reacted with rabbit and goat secondary antibodies and a secondary antibody. Then, protein expression level is confirmed by using an ECL detection reagent (Thermo Scientific, Pierce Biotechnology, USA), and the result is shown in FIG. 6.

Figure 6:
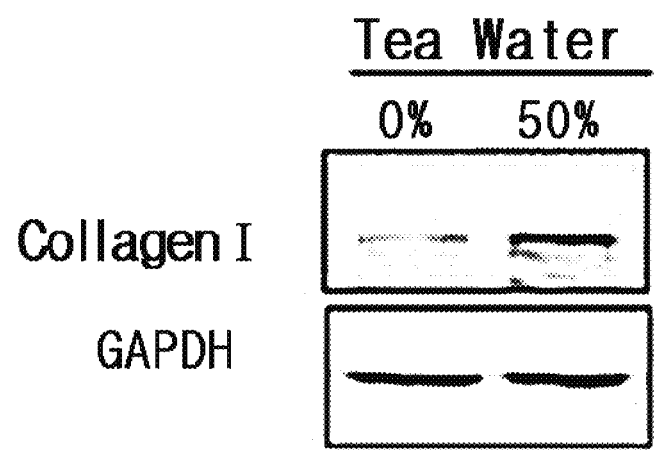
FIG. 6 shows collagen protein expression level by tea water.

As can be seen in FIG. 6, there is no change on the collagen I expression in the cells treated only with the DMEM medium, but the collagen I expression is increased in the cells treated with 50% (v/v) tea water. Namely, the 50% (v/v) tea water has excellent collagen expression promoting effect, and thus, it can be found that it may have excellent effects on suppressing and improving skin wrinkles.

Test Example 5

Confirmation of Protein Expression of Matrix Metalloproteinases (MMPs) and Elastase by Tea Water The human fibroblast cells prepared in (1) of Test Example 3 are added to a 24-well plate and cultured for 24 hours, and then the medium is replaced with a serum-free medium. After 24 hour-starvation, the DMEM medium (Control group) and the DMEM medium prepared in (2) of Test Example 3 containing 50% (v/v) tea water are added thereto, respectively, and then cultured for 120 hours. After culturing, protein of each cell is analyzed by SDS-PAGE analysis method. Quantified 10 μg of protein is subjected to 10% SDS-PAGE, and then reacted with primary antibodies of MMP 1, MMP 3, MMP 9, elastase and GAPDH 1, and then with a secondary antibody. Then, protein expression level is confirmed by using an ECL detection reagent (Thermo Scientific, Pierce Biotechnology, USA), and the results are shown in FIG. 7.

Figure 7:
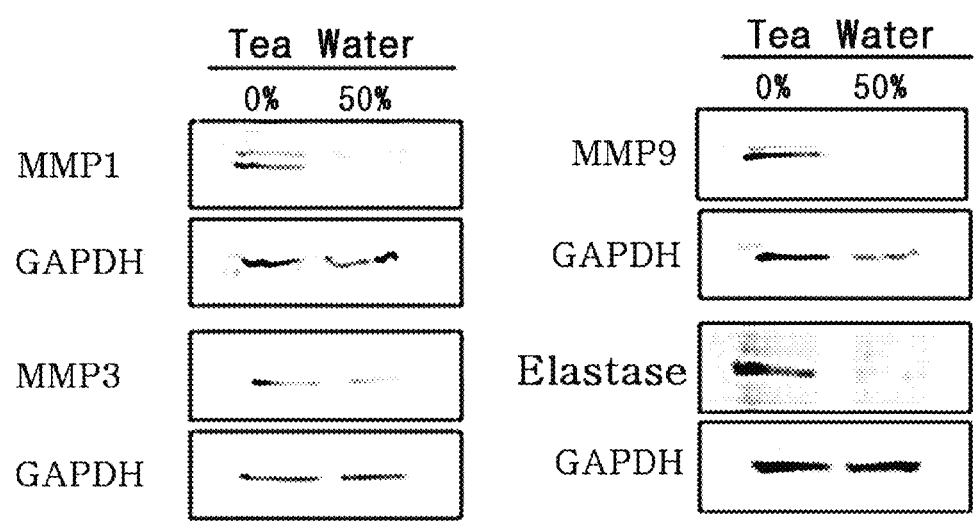
FIG. 7 shows MMP and elastase inhibition level by tea water.

As can be seen in FIG. 7, the expression of MMP 1, MMP 3, MMP 9 and elastase are reduced in the cells treated with the 50% tea water. Thus, it can be found that the 50% (v/v) tea water has effects on suppressing and improving skin wrinkles because it decreases the expressions of MMPs and elastase, which stimulates degradation of the skin collagen.

Test Example 6

Confirmation of Intracellular Collagen Expression by Treatment of Tea Water

Figure 8:
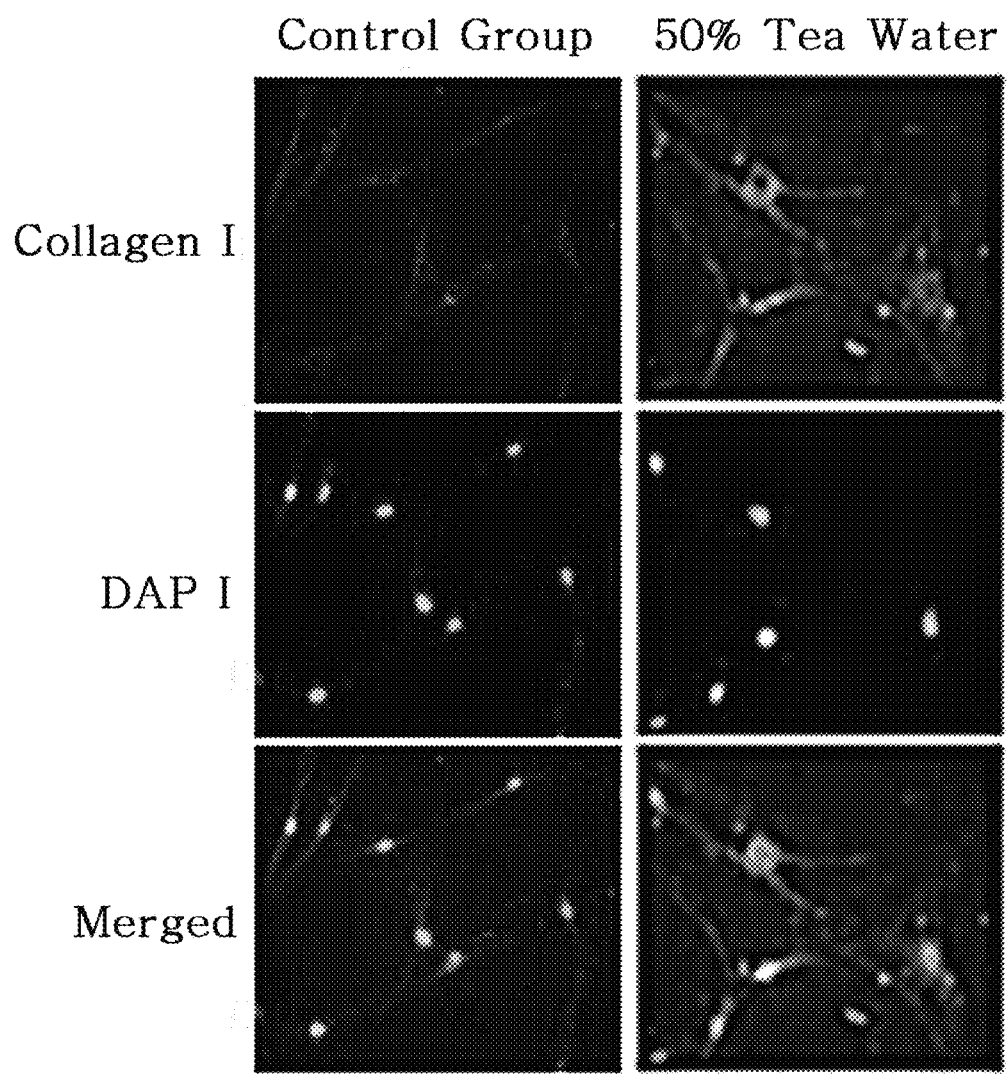
FIG. 8 shows intracellular collagen expression level by tea water.

The human fibroblast cells prepared in (1) of Test Example 3 are added to a 24-well plate and cultured for 24 hours, and then the medium is replaced with a serum-free medium. After 24 hour-starvation, the DMEM medium (Control group) and the DMEM medium prepared in (2) of Test Example 3 containing 50% (v/v) tea water are added thereto, respectively, and then cultured for 120 hours. After culturing, the cells are fixed with 10% paraformaldehyde, and then collagen I antibody is treated for 24 hours. After 24 hours, FITC-labeled secondary antibody (Santa Cruz, Calif., USA) is treated for 2 hours. In order to stain cell nucleus, the cells are treated with 4,6-diamino-2-phenylidole (DAPI; PIERCE, Rockford, USA), mounted, and then observed using a DP70 fluorescence microscope and DP controller software (Olympus Optical Co., Tokyo, Japan). The results are shown in FIG. 8. In FIG. 8, the top images show the collagen expression level, the middle images show the result of DAPI staining, and the bottom images are merged images of the top images and the middle images.

As can be seen in FIG. 8, the collagen I expression level in the cells treated with the 50% (v/v) tea water for 120 hours is higher than the control group. Thus, it can be found that the 50% (v/v) tea water may suppress and improve the skin wrinkles because it stimulates the collagen expression.

Example 2 and Comparative Example 3

Manufacturing of Cosmetic Composition

A mask sheet is manufactured by wetting a sheet with the tea water of Example 1 according to a method commonly employed in the art (Example 2). A mask sheet not containing the tea water is manufactured by the same method with Example 2 (Comparative Example 3).

Test Example 7

Clinical Test about Effect of Tea Water on Wrinkle Reduction

Mask sheets of Example 2 (Test Group) and Comparative Example 3 (Control Group) are applied on the right and left sides of faces of 23 adults aged from 30 to 65 years, respectively, for 8 weeks. Before using Example 2 and Comparative Example 3 and after using for 4 weeks and 8 weeks, wrinkles around eyes of the subjects are measured and evaluated by using a device, and wrinkles of the entire face are evaluated with naked eye by a specialist. Detailed evaluation method and the results are as follows.

(1) Evaluation of Wrinkles Around Eyes Using Device

Firstly, for accurate measurement, let the subject to wash the measuring site with water before measuring, and the temperature and humidity of the skin surface are adapted to environment of the measuring place for 30 min in the waiting room under constant temperature and humidity condition of a temperature of 20 to 25° C. and a humidity of 40 to 60% while restricting fluids. Further, for more objective measurement, the measurement is continued to the same subject and at the same site for each measurement of the test starting point, after 4 weeks and 8 weeks.

Transparency profilometry analysis is conducted to the skin replicas manufactured against the sites where Example 2 and Comparative Example 3 are applied, before use and after 4 weeks and 8 weeks of use, by using a Visiometer SV600 (Courage-Khazaka electronic GmbH, Germany). And, wrinkle parameters R1, R2, R3, R4 and R5 are analyzed.

Specific meanings of the R1, R2, R3, R4 and R5 are as shown in the following Table 5.

TABLE 5

| | | |
|---|---|---|
| R1 | Skin roughness | Difference between the highest value and the lowest value of the wrinkle profile |
| R2 | Maximum roughness | The highest value of five R1 values of the wrinkle profile equally divided into 5 portions |
| R3 | Average roughness | Average of the difference between the highest value and the lowest value in each proportion after equally dividing the wrinkle profile into 5 portions along X-axis (artifacts-removed value compared with R1 and R2) |
| R4 | Smoothness depth | The integrated value of the area formed by the highest value of the wrinkle profile and the profile, divided by the midline length of the profile (Average depth of skin wrinkles) |
| R5 | Arithmetic average roughness | The integrated value of the area formed by the profile and the profile midline, divided by the midline length of the profile |

The results of analyzing R1 (Table 6), R2 (Table 7), R3 (Table 8), R4 (Table 9) and R5 (Table 10) against the test group (Example 2) and the control group (Comparative Example 3) are as shown in the following Table.

TABLE 6

| | | | Test Group (mean ± standard deviation) | Control Group (mean ± standard deviation) |
|---|---|---|---|---|
| | | 0 week | 53.86 ± 11.30 | 45.42 ± 12.54 |
| | | 4$^{th}$ week | 45.45 ± 11.66 | 46.95 ± 17.64 |
| | | 8$^{th}$ week | 37.62 ± 7.94 | 50.51 ± 13.05 |
| Comparison in Group | Significance Probability | 0 week-4$^{th}$ week | 0.026† | 0.677 |
| | | 0 week-8$^{th}$ week | 0.000* | 0.214 |
| Comparison between Groups | Significance Probability | 0 week-4$^{th}$ week | 0.047** | |
| | | 0 week-8$^{th}$ week | 0.000** | |

*$p < 0.05$ (Paired sample's T-test)
†$p < 0.05$ (Wilcoxon signed ranks test)
**$p < 0.05$ (Independent sample's T-test)

TABLE 7

| | | | Test Group (mean ± standard deviation) | Control Group (mean ± standard deviation) |
|---|---|---|---|---|
| | | 0 week | 35.01 ± 6.58 | 30.19 ± 7.80 |
| | | 4$^{th}$ week | 28.13 ± 4.87 | 27.98 ± 6.59 |
| | | 8$^{th}$ week | 23.53 ± 3.99 | 30.76 ± 8.05 |
| Comparison in Group | Significance Probability | 0 week-4$^{th}$ week | 0.000* | 0.219 |
| | | 0 week-8$^{th}$ week | 0.000* | 0.788 |
| Comparison between Groups | Significance Probability | 0 week-4$^{th}$ week | 0.051 | |
| | | 0 week-8$^{th}$ week | 0.000** | |

*$p < 0.05$ (Paired sample's T-test)
**$p < 0.05$ (Independent sample's T-test)

TABLE 8

|  |  |  | Test Group (mean ± standard deviation) | Control Group (mean ± standard deviation) |
|---|---|---|---|---|
|  | 0 week |  | 23.31 ± 4.02 | 20.37 ± 5.15 |
|  | 4$^{th}$ week |  | 18.85 ± 2.58 | 18.88 ± 4.46 |
|  | 8$^{th}$ week |  | 16.24 ± 2.58 | 20.67 ± 4.87 |
| Comparison in Group | Significance Probability | 0 week-4$^{th}$ week | 0.000* | 0.194 |
|  |  | 0 week-8$^{th}$ week | 0.000* | 0.831 |
| Comparison between Groups | Significance Probability | 0 week-4$^{th}$ week | 0.044# | |
|  |  | 0 week-8$^{th}$ week | 0.000** | |

*$p < 0.05$ (Paired sample's T-test)
**$p < 0.05$ (Independent sample's T-test)
$p < 0.05$ (Mann-Whitney U test)

TABLE 9

|  |  |  | Test Group (mean ± standard deviation) | Control Group (mean ± standard deviation) |
|---|---|---|---|---|
|  | 0 week |  | 23.00 ± 6.96 | 19.03 ± 6.53 |
|  | 4$^{th}$ week |  | 20.32 ± 7.22 | 21.15 ± 9.71 |
|  | 8$^{th}$ week |  | 16.27 ± 4.49 | 21.25 ± 6.36 |
| Comparison in Group | Significance Probability | 0 week-4$^{th}$ week | 0.294 | 0.322 |
|  |  | 0 week-8$^{th}$ week | 0.000† | 0.275 |
| Comparison between Groups | Significance Probability | 0 week-4$^{th}$ week | 0.110 | |
|  |  | 0 week-8$^{th}$ week | 0.001** | |

†$p < 0.05$ (Wilcoxon signed ranks test)
**$p < 0.05$ (Independent sample's T-test)

TABLE 10

|  |  |  | Test Group (mean ± standard deviation) | Control Group (mean ± standard deviation) |
|---|---|---|---|---|
|  | 0 week |  | 10.16 ± 3.18 | 8.38 ± 3.37 |
|  | 4$^{th}$ week |  | 8.74 ± 3.13 | 9.21 ± 4.96 |
|  | 8$^{th}$ week |  | 7.09 ± 2.13 | 9.97 ± 3.53 |
| Comparison in Group | Significance Probability | 0 week-4$^{th}$ week | 0.162 | 0.429 |
|  |  | 0 week-8$^{th}$ week | 0.000* | 0.115 |
| Comparison between Groups | Significance Probability | 0 week-4$^{th}$ week | 0.102 | |
|  |  | 0 week-8$^{th}$ week | 0.000** | |

*$p < 0.05$ (Paired sample's T-test)
**$p < 0.05$ (Independent sample's T-test)

Figure 9:
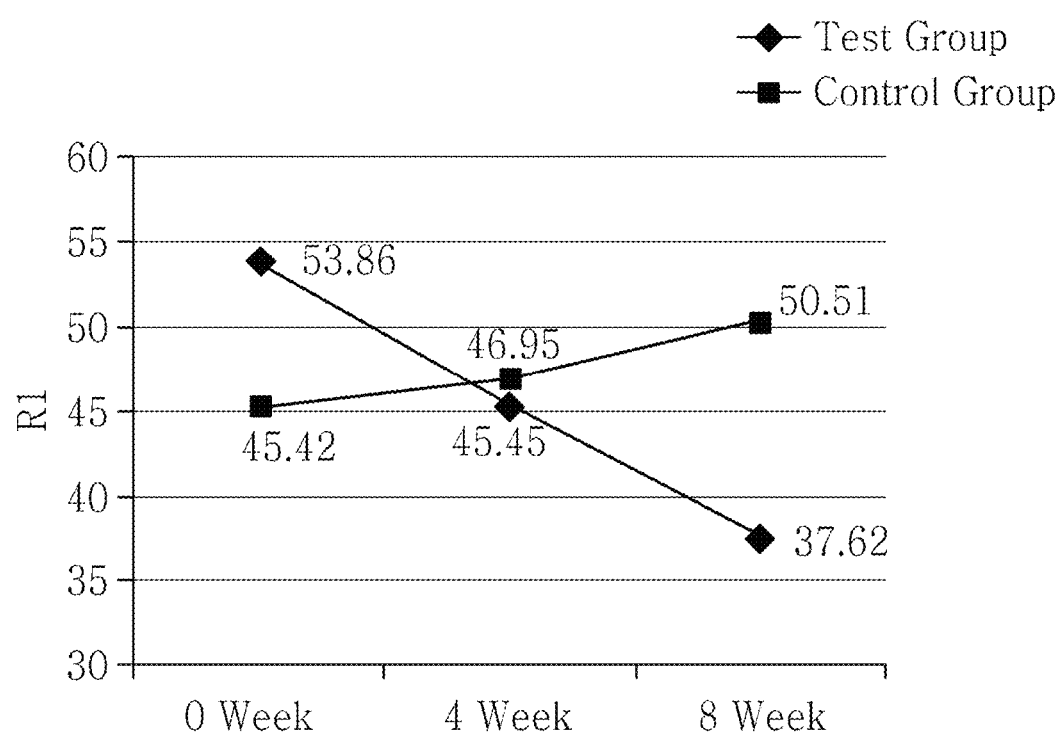
FIG. 9 is a graph showing variation of skin wrinkle parameter, R1, by a composition containing tea water and a composition not containing the tea water.
Figure 10:
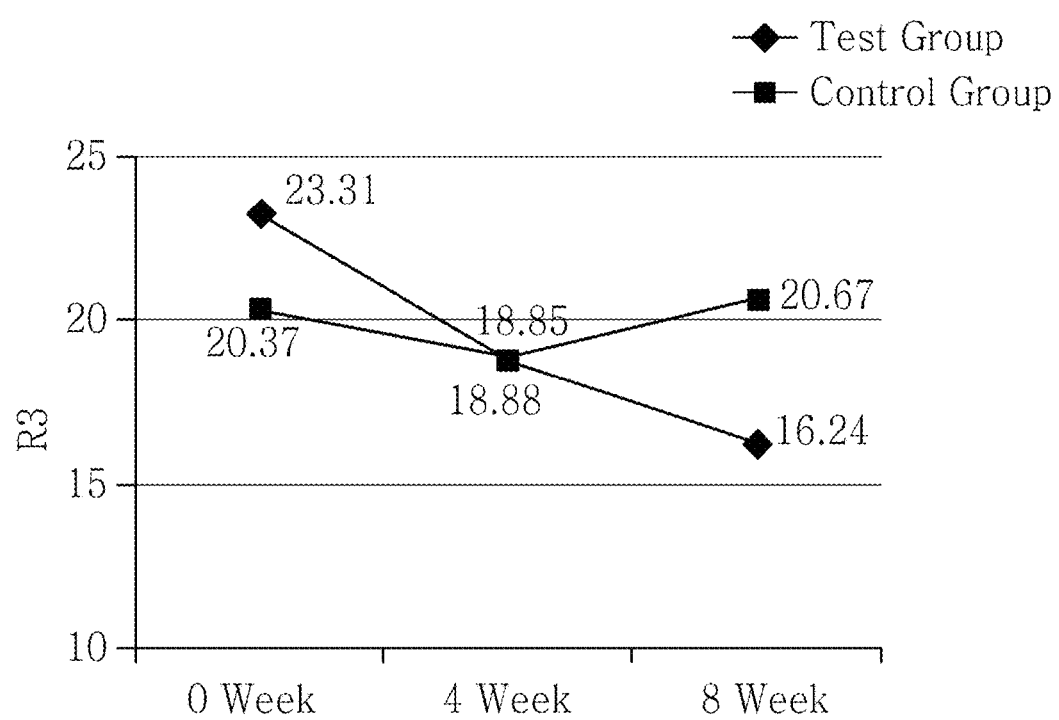
FIG. 10 is a graph showing variation of skin wrinkle parameter, R3, by a composition containing tea water and a composition not containing the tea water.

Further, the result of measuring R1 and R3 against the Test group (Example 2) and the control group (Comparative Example 3) are shown in FIG. 9 and FIG. 10, respectively.

As shown in the above results, in the case of using the mask sheet containing tea water of Example 2, all wrinkle parameters R1, R2, R3, R4 and R5 values are significantly reduced, but in the case of using the mask sheet not containing tea water of Comparative Example 3, the R1, R2, R3, R4 and R5 values are not changed or increased. Accordingly, through the wrinkle test using a device, it can be found that in the case of using a cosmetic composition containing tea water, the composition may effectively reduce skin wrinkles.

(2) Evaluation of Wrinkles with Naked Eye by Specialist

Before using Example 2 and Comparative Example 3, after 4 weeks and 8 weeks of using thereof, two specialists score the degree of wrinkles of a subject according to global photodamage score (see Table 3 and FIG. 1 of Br J Dermatol. 2010; 162(3):497-502). Score evaluation standard is as shown in the following Table 11, and the evaluation results are shown in Table 12. If there is difference between the scores of the two specialists, the lower score is selected.

TABLE 11

| Score | Degree of Wrinkle |
|---|---|
| 0 | None |
| 1 | None/Mild |
| 2 | Mild |
| 3 | Mild/Moderate |
| 4 | Moderate |
| 5 | Moderate/Severe |
| 6 | Severe |
| 7 | Very Severe |

TABLE 12

| | | | Test Group (mean ± standard deviation) | Control Group (mean ± standard deviation) |
|---|---|---|---|---|
| | 0 week | | 2.96 ± 0.64 | 2.91 ± 0.67 |
| | 4th week | | 2.61 ± 0.66 | 2.91 ± 0.67 |
| | 8th week | | 2.22 ± 0.74 | 2.74 ± 0.75 |
| Comparison in Group | Significance Probability | 0 week-4th week | 0.005† | 1.000 |
| | | 0 week-8th week | 0.000† | 0.046† |
| Comparison between Groups | Significance Probability | 0 week-4th week | 0.002# | |
| | | 0 week-8th week | 0.000# | |

†$p < 0.05$ (Wilcoxon signed ranks test)
$p < 0.05$ (Mann-Whitney U test)

As can be seen in the above results, the evaluation scores of the test group evaluated with naked eye by the specialists are gradually reduced with time, and the scores of the control group are not reduced until 8th week. As the result of analyzing this by Wilcoxon signed ranks test as a nonparametric test according to normality test, statistically significant change of significant probability $p<0.05$ (significant level: 5%) is observed in the test group from 0 week to 4th week and from 0 week to 8th week. However, statistically significant change of significant probability $p<0.05$ (significant level: 5%) is observed in the control group only from 0 week to 8th week. Further, as the result of analyzing whether there is difference on the variation of wrinkle score between the test group and the control group, by Mann-Whitney U test as a nonparametric test according to normality test, statistically significant change of significant probability $p<0.05$ (significant level: 5%) is observed between the test group and the control group from both 0 week to 4th week and from 0 week to 8th week.

Namely, through the evaluation with naked eye by the specialists, it can be found that when using the cosmetic composition containing tea water, skin wrinkles may be effectively reduced.

What is claimed is:

1. A method for improving or suppressing skin wrinkles comprising topically administering to a subject in need of improving or suppressing skin wrinkles an effective amount of a composition comprising tea water, which is derived from fresh tea leaves in which enzymes are inactivated, wherein the tea water is a distillate which is obtained by distilling a tea juice obtained by extracting the fresh tea leaves without any solvent.

2. The method according to claim 1, wherein the composition comprises the tea water in an amount of about 10 to about 90 volume % (v/v %), based on the total volume of the composition.

3. The method according to claim 1, wherein the tea water inhibits break down of collagen and elastin.

4. The method according to claim 1, wherein the tea water comprises non-ionic tea water.

5. The method according to claim 1, wherein the tea water comprises tea water satisfying at least one of linalool concentration of 5 μg/ml or less, hexanol concentration of 0.2 μg/ml or less and z-3-hexenol concentration of 0.2 μg/ml or less.

6. The method according to claim 1, wherein the composition is a cosmetic composition.

7. The method according to claim 1, wherein the composition is a pharmaceutical composition.

* * * * *